(12) United States Patent
Marshall et al.

(10) Patent No.: US 8,905,971 B2
(45) Date of Patent: Dec. 9, 2014

(54) INJECTION METHOD AND APPARATUS

(75) Inventors: Jeremy Marshall, Jericho (GB); Mark Eaton, Witney (GB)

(73) Assignee: Owen Mumford, Ltd., Woodstock, Oxfordshire (GB)

( * ) Notice: Subject to any disclaimer, the term of this patent is extended or adjusted under 35 U.S.C. 154(b) by 213 days.

(21) Appl. No.: 12/561,320

(22) Filed: Sep. 17, 2009

(65) Prior Publication Data
US 2010/0069845 A1 Mar. 18, 2010

Related U.S. Application Data

(63) Continuation of application No. 11/598,969, filed on Nov. 14, 2006, now abandoned.

(30) Foreign Application Priority Data

Dec. 2, 2005 (GB) .................................. 0524604.6

(51) Int. Cl.
*A61M 5/20* (2006.01)
*A61M 5/315* (2006.01)

(52) U.S. Cl.
CPC ......... *A61M 5/31583* (2013.01); *A61M 5/3156* (2013.01); *A61M 5/31543* (2013.01); *A61M 5/31535* (2013.01); *A61M 5/31553* (2013.01); *A61M 5/20* (2013.01); *A61M 2205/6081* (2013.01); *A61M 5/3155* (2013.01); *A61M 2205/583* (2013.01)
USPC ....................................................... 604/135

(58) Field of Classification Search
USPC .......... 604/187, 189, 207, 134, 135; 600/135; 606/182
See application file for complete search history.

(56) References Cited

U.S. PATENT DOCUMENTS 930,477 A 8/1909 Hudson
3,620,209 A 11/1971 Kravitz
(Continued)

FOREIGN PATENT DOCUMENTS

DE 1049188 1/1959
DE 3730469 6/1988
(Continued)

OTHER PUBLICATIONS

JP 2005185712A Shiga Moulding, WPI Abstract Accession No. 2005-464425 and EPO DOC Abstract.
(Continued)

*Primary Examiner* — Nathan R Price
(74) *Attorney, Agent, or Firm* — Kilpatrick Townsend & Stockton LLP

(57) ABSTRACT

A pen-type injector for receiving a medication containing member. The injector comprises a housing 1 and a torsion spring 4 contained within the housing and coupled to a drive member 8. A dose setting knob 2 is coupled to the spring 4, and rotatably coupled to the housing 1 such that rotation of the knob relative to the housing in a first direction results in compression or twisting of the spring. A user actuable trigger 12 is provided for releasing the spring 4 to push the drive member 8 through the housing 1. A user actuable button 6 is coupled to the housing 1 for axial motion relative thereto, said button 6 being coupled to the torsion spring 4 to cause the spring to unwind or expand in discrete steps with each press of the button.

16 Claims, 12 Drawing Sheets

(56) References Cited

U.S. PATENT DOCUMENTS

| | | | |
|---|---|---|---|
| 3,659,608 A | 5/1972 | Perry |
| 3,698,395 A | 10/1972 | Hasson |
| 3,760,809 A | 9/1973 | Campbell |
| 4,442,836 A | 4/1984 | Meinecke et al. |
| 4,449,529 A | 5/1984 | Burns et al. |
| 4,462,405 A | 7/1984 | Ehrlich |
| 4,517,978 A | 5/1985 | Levin et al. |
| D281,383 S | 11/1985 | Beach |
| 4,553,541 A | 11/1985 | Burns |
| 4,565,545 A | 1/1986 | Suzuki |
| 4,646,753 A | 3/1987 | Nugent |
| 4,653,513 A | 3/1987 | Dombrowski |
| 4,820,287 A | 4/1989 | Leonard |
| RE32,922 E | 5/1989 | Levin et al. |
| 4,858,607 A | 8/1989 | Jordan et al. |
| 4,902,279 A | 2/1990 | Schmidtz et al. |
| 4,917,243 A | 4/1990 | Abrams et al. |
| 4,967,763 A | 11/1990 | Nugent et al. |
| 5,026,388 A | 6/1991 | Ingalz |
| 5,046,612 A | 9/1991 | Mostarda et al. |
| D322,211 S | 12/1991 | Gary |
| 5,104,380 A | 4/1992 | Holman et al. |
| 5,104,388 A | 4/1992 | Quackenbush |
| 5,116,353 A | 5/1992 | Green |
| D327,214 S | 6/1992 | Stuart |
| D327,321 S | 6/1992 | Russell et al. |
| 5,147,306 A | 9/1992 | Gubich |
| 5,201,324 A | 4/1993 | Swierczek |
| 5,226,895 A | 7/1993 | Harris |
| 5,226,896 A | 7/1993 | Harris |
| 5,242,421 A | 9/1993 | Chan et al. |
| 5,279,585 A * | 1/1994 | Balkwill ............... 604/207 |
| 5,308,340 A | 5/1994 | Harris |
| 5,320,609 A * | 6/1994 | Haber et al. ............. 604/135 |
| 5,324,303 A | 6/1994 | Strong et al. |
| 5,353,806 A | 10/1994 | Heinzelman et al. |
| 5,364,362 A | 11/1994 | Schultz |
| 5,368,047 A | 11/1994 | Suzuki et al. |
| 5,383,865 A | 1/1995 | Michell |
| 5,402,798 A | 4/1995 | Swierczek et al. |
| 5,423,847 A | 6/1995 | Strong et al. |
| 5,439,453 A | 8/1995 | Kashanci |
| 5,439,473 A | 8/1995 | Jorgensen |
| D362,064 S | 9/1995 | Smick |
| 5,454,828 A | 10/1995 | Schraga |
| 5,472,433 A | 12/1995 | Suzuki |
| 5,487,748 A | 1/1996 | Marshall et al. |
| 5,514,097 A | 5/1996 | Knauer |
| 5,527,296 A | 6/1996 | Kashanchi |
| 5,529,581 A | 6/1996 | Cusack |
| 5,547,702 A | 8/1996 | Gleisner |
| 5,552,117 A | 9/1996 | Burns |
| 5,554,166 A | 9/1996 | Lange et al. |
| 5,569,286 A | 10/1996 | Peckham et al. |
| 5,580,794 A | 12/1996 | Allen |
| 5,591,136 A | 1/1997 | Gabriel |
| 5,601,588 A | 2/1997 | Tonomura et al. |
| 5,609,577 A | 3/1997 | Haber et al. |
| 5,611,809 A | 3/1997 | Marshall et al. |
| 5,613,978 A | 3/1997 | Harding |
| 5,626,566 A | 5/1997 | Petersen et al. |
| 5,628,764 A | 5/1997 | Schraga |
| 5,707,384 A | 1/1998 | Kim |
| 5,709,699 A | 1/1998 | Warner |
| 5,725,508 A | 3/1998 | Chanoch et al. |
| 5,730,753 A | 3/1998 | Morita |
| 5,743,889 A | 4/1998 | Sams |
| 5,749,886 A | 5/1998 | Abidin et al. |
| 5,797,942 A | 8/1998 | Schraga |
| 5,827,232 A | 10/1998 | Chanoch et al. |
| 5,837,546 A | 11/1998 | Allen et al. |
| 5,871,494 A | 2/1999 | Simons et al. |
| 5,872,713 A | 2/1999 | Douglas et al. |
| 5,879,311 A | 3/1999 | Duchon et al. |
| 5,879,367 A | 3/1999 | Latterell et al. |
| 5,910,147 A | 6/1999 | Rosenberg et al. |
| 5,916,230 A | 6/1999 | Brenneman et al. |
| 5,951,493 A | 9/1999 | Douglas et al. |
| 6,004,297 A | 12/1999 | Steenfeldt-Jensen et al. |
| D421,214 S | 2/2000 | Koros et al. |
| 6,053,930 A | 4/2000 | Ruppert |
| 6,056,765 A | 5/2000 | Bajaj et al. |
| 6,071,249 A | 6/2000 | Cunningham et al. |
| 6,071,250 A | 6/2000 | Douglas et al. |
| 6,093,156 A | 7/2000 | Cunningham et al. |
| 6,106,539 A | 8/2000 | Fortier |
| 6,132,449 A | 10/2000 | Lum et al. |
| 6,136,013 A | 10/2000 | Marshall et al. |
| 6,152,942 A | 11/2000 | Brenneman et al. |
| 6,159,181 A | 12/2000 | Crossman et al. |
| 6,197,040 B1 | 3/2001 | LeVaughn et al. |
| 6,203,504 B1 | 3/2001 | Latterell et al. |
| 6,210,420 B1 | 4/2001 | Mauze et al. |
| 6,248,095 B1 | 6/2001 | Giambattista et al. |
| 6,261,245 B1 | 7/2001 | Kawai et al. |
| D446,107 S | 8/2001 | Carter |
| 6,277,097 B1 | 8/2001 | Mikkelsen et al. |
| 6,283,982 B1 | 9/2001 | Levaughn et al. |
| 6,306,152 B1 | 10/2001 | Verdonk et al. |
| 6,319,209 B1 | 11/2001 | Kriz |
| 6,332,871 B1 | 12/2001 | Douglas et al. |
| 6,419,661 B1 | 7/2002 | Kuhr et al. |
| 6,464,649 B1 | 10/2002 | Duchon et al. |
| 6,491,709 B2 | 12/2002 | Sharma et al. |
| D470,391 S | 2/2003 | Adams |
| 6,540,762 B1 | 4/2003 | Bertling |
| 6,558,402 B1 | 5/2003 | Chelak et al. |
| 6,589,210 B1 | 7/2003 | Rolfe |
| 6,607,508 B2 | 8/2003 | Knauer |
| 6,616,640 B2 | 9/2003 | Chen et al. |
| 6,645,219 B2 | 11/2003 | Roe |
| 6,706,049 B2 | 3/2004 | Moerman |
| 6,755,805 B1 | 6/2004 | Reid |
| 6,899,698 B2 * | 5/2005 | Sams ............... 604/211 |
| 6,899,699 B2 | 5/2005 | Enggaard |
| 6,902,554 B2 | 6/2005 | Hunter |
| 6,945,961 B2 | 9/2005 | Miller et al. |
| D516,218 S | 2/2006 | Larocca |
| 7,112,187 B2 * | 9/2006 | Karlsson ............... 604/187 |
| D529,792 S | 10/2006 | Klein et al. |
| 7,241,278 B2 | 7/2007 | Moller |
| 7,244,266 B2 | 7/2007 | Garthe et al. |
| 8,372,103 B2 | 2/2013 | Marshall |
| 2002/0004196 A1 | 1/2002 | Whitson |
| 2002/0013602 A1 | 1/2002 | Huttner |
| 2002/0016606 A1 | 2/2002 | Moerman |
| 2002/0029058 A1 | 3/2002 | Levaughn et al. |
| 2002/0082521 A1 | 6/2002 | Sharma et al. |
| 2002/0130042 A1 | 9/2002 | Moerman et al. |
| 2002/0169393 A1 | 11/2002 | Cunningham et al. |
| 2002/0198444 A1 | 12/2002 | Uchigaki et al. |
| 2003/0050655 A1 | 3/2003 | Roe |
| 2003/0195540 A1 | 10/2003 | Moerman |
| 2004/0098010 A1 | 5/2004 | Davison |
| 2004/0158271 A1 | 8/2004 | Hamamoto |
| 2004/0162573 A1 | 8/2004 | Kheiri |
| 2005/0038465 A1 | 2/2005 | Shraga |
| 2005/0197625 A1 | 9/2005 | Haueter et al. |
| 2006/0129172 A1 | 6/2006 | Crossman et al. |
| 2006/0229652 A1 | 10/2006 | Lio et al. |
| 2006/0259058 A1 | 11/2006 | Schiff et al. |
| 2007/0129687 A1 | 6/2007 | Marshall et al. |
| 2007/0156163 A1 | 7/2007 | Davison et al. |
| 2007/0162063 A1 | 7/2007 | Marshall et al. |
| 2007/0225742 A1 | 9/2007 | Abe et al. |
| 2007/0233166 A1 | 10/2007 | Stout |
| 2007/0299394 A1 | 12/2007 | Rolfe et al. |
| 2008/0033469 A1 | 2/2008 | Winheim et al. |
| 2008/0306446 A1 | 12/2008 | Markussen |
| 2009/0054839 A1 * | 2/2009 | Moller et al. ............... 604/135 |
| 2009/0287237 A1 | 11/2009 | Nicholls |
| 2010/0004560 A1 | 1/2010 | Davison |
| 2010/0179485 A1 * | 7/2010 | Radmer et al. ............... 604/189 |

(56) References Cited

U.S. PATENT DOCUMENTS

| | | |
|---|---|---|
| 2011/0313440 A1 | 12/2011 | Nicholls et al. |
| 2012/0253231 A1 | 10/2012 | Davison |
| 2013/0245497 A1 | 9/2013 | Davison |

FOREIGN PATENT DOCUMENTS

| | | |
|---|---|---|
| DE | 102004045043 | 4/2006 |
| EP | 0097748 | 1/1984 |
| EP | 0137975 | 4/1985 |
| EP | 0295075 | 12/1988 |
| EP | 0327910 | 8/1989 |
| EP | 338806 | 10/1989 |
| EP | 0450905 | 10/1991 |
| EP | 0555554 | 8/1993 |
| EP | 0783868 | 7/1997 |
| EP | 897728 | 2/1999 |
| EP | 0925021 | 6/1999 |
| EP | 0956874 | 11/1999 |
| EP | 1174083 | 1/2002 |
| EP | 1204371 | 5/2002 |
| EP | 1507566 | 11/2003 |
| EP | 1570792 A1 | 9/2005 |
| EP | 1785090 | 5/2007 |
| EP | 1819382 | 8/2007 |
| FR | A2649893 | 1/1991 |
| GB | 2440119 A | 1/2008 |
| GB | 2465391 | 5/2010 |
| JP | 2001507250 | 6/2001 |
| JP | 2007501043 | 1/2007 |
| JP | 2008507373 | 3/2008 |
| JP | 2009543646 | 12/2009 |
| WO | WO8504089 | 9/1985 |
| WO | WO8808724 | 11/1988 |
| WO | WO9108786 | 6/1991 |
| WO | WO9110460 | 7/1991 |
| WO | WO9607443 | 3/1996 |
| WO | WO9704707 | 2/1997 |
| WO | WO9708986 | 3/1997 |
| WO | WO9806331 | 2/1998 |
| WO | 9811821 | 3/1998 |
| WO | WO9906100 | 2/1999 |
| WO | WO9938554 | 8/1999 |
| WO | WO0113794 | 3/2001 |
| WO | WO0128423 | 4/2001 |
| WO | WO0162150 | 8/2001 |
| WO | WO0172361 | 10/2001 |
| WO | WO0195806 | 12/2001 |
| WO | WO0209575 | 2/2002 |
| WO | WO0230495 | 4/2002 |
| WO | WO02053214 | 7/2002 |
| WO | WO03097133 | 11/2003 |
| WO | WO2004002556 | 1/2004 |
| WO | 2004082748 A1 | 9/2004 |
| WO | WO2004093940 | 11/2004 |
| WO | 2005013825 A1 | 2/2005 |
| WO | 2005020816 | 3/2005 |
| WO | 2006013532 | 2/2006 |
| WO | WO2006045526 | 5/2006 |
| WO | WO2006045528 | 5/2006 |
| WO | WO2006045529 | 5/2006 |
| WO | 2006058654 | 6/2006 |
| WO | WO2006092309 | 9/2006 |
| WO | 2008009984 A1 | 1/2008 |
| WO | 2010055330 | 5/2010 |

OTHER PUBLICATIONS

'Blood Glucose Concentrations of Arm and Finger During Dynamic Glucose Conditions' by Ete Z. Szuts, Ph.D., *Diabetes Technology & Therapeutics*, 4(1):3-11 (2002).
'Vacuum-Assisted Lancing of the Forearm: An Effective and Less Painful Approach to Blood Glucose Monitoring' by David D. Cunningham, *Diabetes Technology & Therapeutics*, 2(4):541-548 (2000).
Ascensia® MICROLET® VACULANCE® Lancing Device; product information brochure; www.bayercarediabetes.com; printed Feb. 13, 2003 (03 pages).
Ascensia®MICROLET®VACULANCE® Lancing Device; product information brochure for Easy Lancing on Alternative Sites; www.bayercarediabetes.com; printed Feb. 13, 2004 (02 pages).
At Last™ Blood Glucose System User's Manual, AMIRA (c) 1999.
TheraSense™ The Technology of Caring Owner's Booklet (date unknown).
Glucose® Automatic Lancing Device / An Illustrated User Procedure.
Davis, Opening Up the Gate Control Theory, Nurs. Stand., 7(45)25-7 (1993).
Apkarian, et al., Heat-induced Pain Diminishes Vibrotactile Perception: A Touch Gate, Somatosens Mot. Res., 11(3):259-67 (1994).
Melzack, 'From the Gate to the Neuromatrix,' Pain Supplement 6 S121-S126 (1999), Published by Elsevier Science B.V.
Barnhill, et al., Using Pressure to Decrease the Pain of Intramuscular Injections, Journal of Pain and Symptom Management, 12:52-58 (1996), Published by Elevier, New York, New York.
Search Report in related Application No. GB0409354.8.
AutopenTM Owen Mumford Ltd. Of Woodstock, UK, one page (May 7, 2007) http://www.owenmumford.com.
Search Report in related Application No. GB0600523.5.
Office Action dated Mar. 13, 2009 in related U.S. Appl. No. 11/712,754.
Office Action dated Dec. 30, 2008 in related U.S. Appl. No. 11/598,969.
Office Action dated Apr. 17, 2009 in related U.S. Appl. No. 11/598,969.
Office Action dated Nov. 10, 2008 in related U.S. Appl. No. 11/651,241.
Response dated May 8, 2009 in related U.S. Appl. No. 11/651,241.
Office Action dated Aug. 10, 2009 in related U.S. Appl. No. 11/651,241.
Response dated Oct. 12, 2009 in related U.S. Appl. No. 11/651,241.
Interview Summary dated Nov. 9, 2009 in related U.S. Appl. No. 11/651,241.
Advisory Action dated Nov. 16, 2009 in related U.S. Appl. No. 11/651,241.
Response dated Dec. 16, 2009 in related U.S. Appl. No. 11/651,241.
Office Communication dated Dec. 29, 2009 in related U.S. Appl. No. 11/651,241.
Supplemental Response dated Jan. 28, 2010 in related U.S. Appl. No. 11/651,241.
Office Action dated Nov. 24, 2010 in related U.S. Appl. No. 11/651,241.
Office Action dated May 11, 2006 in related U.S. Appl. No. 10/635,806.
Response dated Oct. 10, 2006 in related U.S. Appl. No. 10/635,806.
Office Action dated Nov. 6, 2006 in related U.S. Appl. No. 10/635,806.
Response dated Jan. 5, 2007 in related U.S. Appl. No. 10/635,806.
Advisory Action dated Jan. 25, 2007 in related U.S. Appl. No. 10/635,806.
U.S. Appl. No. 09/959,262 filed Oct. 22, 2001.
Office Action dated Jul. 21, 2003 in related U.S. Appl. No. 09/959,262.
Response dated Oct. 14, 2003 in related U.S. Appl. No. 09/959,262.
Office Action dated Nov. 4, 2003 in related U.S. Appl. No. 09/959,262.
Owen Mumford Brochure entitled "AutojectMini" two pages (1993).
Owen Mumford Drawing No. AJ525, one page (1995).
Anapen® Patient Information Leaflet Celltech, two pages (2002).
Clexane® HandyPEN®Brochure Clexane 20, two pages (1999).
Serono Home Care list of contents and related invoice, two pages (2002).
Webpage ENBREL.ca: How to Use ENBREL SureClick Autoinjector: Introduction, five pages) accessed 2009 http://www.enbrel.ca/en/about/howUseSureClick/intro.html.
SimpleJect™ Auto-Inject System Directions for Use Brochure, 8 pages (2001).
SimpleJect™ Drawing #AJ/1700/11/0024/01, 3 pages (1999).

(56) References Cited

OTHER PUBLICATIONS

Owen Mumford Advanced New autoject2 Brochure, three pages (1995).
Knoll/Abbott Drawing DP321 and invoice, three pages (1999).
AMGEN Aranesp® Information Leaflet, two pages (2005).
Office Action dated Jun. 21, 2013 in U.S. Appl. No. 13/129,596.
Response dated Sep. 23, 2013 in U.S. Appl. No. 13/129,596.
Office Action dated Oct. 4, 2013 in U.S. Appl. No. 13/129,596.
Office Action dated Sep. 5, 2013 in U.S. Appl. No. 13/888,397.
Japanese Patent Application No. 2011-543812, Non-Final Office Action, mailed Jan. 14, 2014 (4 pages).
Notice of Allowance dated Nov. 27, 2012 in U.S. Appl. No. 11/651,241.
Office Action dated Nov. 7, 2012 in U.S. Appl. No. 13/495,316.
Response dated Apr. 13, 2012 in U.S. Appl. No. 12/557,833.
Office Action dated May 11, 2012 in U.S. Appl. No. 12/557,833.
U.S. Appl. No. 13/129,596, Non-Final Office Action mailed on Apr. 21, 2014, 11 pages.
Response dated Sep. 8, 2011 in related U.S. Appl. No. 11/651,241.
Office Action dated Aug. 12, 2011 in related U.S. Appl. No. 12/557,833.
International Search Report dated Feb. 19, 2010 in International Application No. PCT/GB2009/051510.
Search Report dated Oct. 13, 2009 in Application No. GB0820969.4.
Office Action dated Aug. 12, 2011 in U.S. Appl. No. 12/557,833.
Office Action dated Dec. 13, 2011 in U.S. Appl. No. 12/557,833.
Notice of Allowance dated Nov. 23, 2011 in U.S. Appl. No. 11/651,241.
RCE dated Dec. 19, 2011 in U.S. Appl. No. 11/651,241.
Search Report dated Sep. 6, 2004 in Application No. GB0409354.8.
Response dated Feb. 24, 2011 in related U.S. Appl. No. 11/651,241.
Office Action dated Jun. 8, 2011 in related U.S. Appl. No. 11/651,241.

* cited by examiner

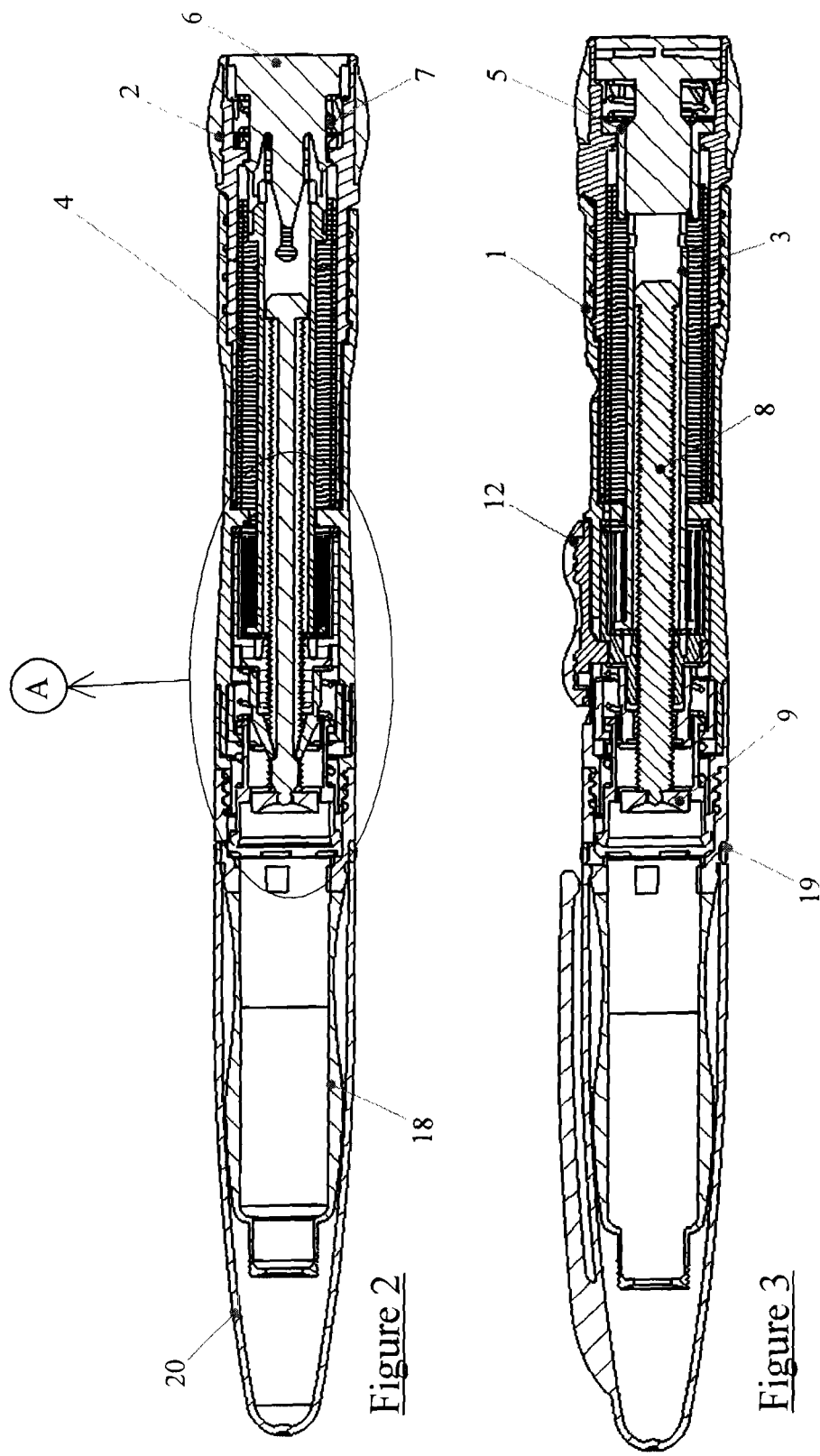

US 8,905,971 B2

INJECTION METHOD AND APPARATUS

RELATED APPLICATION DATA

This application claims priority to United Kingdom Patent Application No. GB0524604.6 filed on Dec. 2, 2005, the contents of which are incorporated herein by reference.

FIELD OF THE INVENTION

The present invention relates to an injection method and apparatus, and more particularly to an injection method and apparatus which provides for automatic medication delivery and for variable dose setting.

BACKGROUND

U.S. Pat. No. 5,104,380 describes a generally pen-like syringe which incorporates a dose metering device provided by a cap or "dose knob" which is rotatable with respect to the pen body to a position related to the dose of medication to be injected. Rotation loads (by twisting) a coil spring which is prevented from unwinding by cooperating teeth. The user disengages the ratchet teeth by means of a sliding trigger coupled to the outside of the pen body, resulting in the unwinding of the spring. This in turn causes rotation of a drive gear which is coupled to a syringe plunger via a quick pitch screw thread. Rotation of the gear results in axial movement of the plunger through the pen body. The plunger acts on a "bung" of a medicament containing cartridge, driving medicament from the cartridge as it travels. The structure of the syringe of U.S. Pat. No. 5,104,380 is such that, once a dose has been set by a user dialing the dose knob to a given position, the user cannot reduce the setting by winding the dose knob in the reverse direction. If the dose has been overset, the user must activate the trigger to expel the set dose, and redial the correct dose.

WO02/053214 describes a syringe comprising a similar dose setting mechanism. The design described in this document is claimed to allow the dose knob to be rotated in the reverse direction to allow an overset dose to be reduced.

According to a first aspect of the present invention there is provided medication delivery apparatus comprising:
 a housing for receiving a medication containing member;
 a drive member mounted within the housing for engaging with the medication containing member and moveable axially within the housing;
 a spring contained within the housing and coupled to the drive member;
 a dose setting knob coupled to said spring, and rotatably coupled to the housing such that rotation of the knob relative to the housing in a first direction results in compression or twisting of the spring;
 a user actuable trigger for releasing the spring to push the drive member through the housing; and
 a user actuable button coupled to said housing for axial motion relative thereto, said button being coupled to said spring to cause the spring to unwind or expand without causing any substantial movement of said drive member.

Preferably, actuation of said button causes said spring to unwind or expand in discrete steps with each press of the button In an embodiment of the present invention, the apparatus further comprises a drive shaft extending through the housing, the drive shaft being coupled via a ratchet mechanism to a drive element, and the drive element being coupled to said drive member, whereby rotation of the drive element gives rise to axial movement of the drive member. Said dose setting knob is coupled to the drive shaft for rotation therewith when the user actuable button is in a released position, and is decoupled from the drive shaft when the button is in a depressed position whereupon the dose knob is able to rotate relative to the drive shaft.

Said user actuable trigger is configured to release said drive element for rotation by the spring when the trigger is actuated, and to secure the drive element when the trigger is in its resting state.

Said ratchet mechanism preferably comprises two complimentary sets of teeth, a first set formed on an end of the drive shaft and a second formed on the drive element. With the trigger in its resting state, the teeth of the drive shaft are able to ride over the teeth of the drive unit to allow rotation of the drive shaft relative to the drive element when the dose knob is rotated in a dose setting direction.

Preferably, said user actuable button is coupled to the drive shaft for rotation therewith. The drive shaft comprises means for locking the drive shaft to the dose knob, which means is released when the button is depressed by a user. The locking means may comprise one or more teeth for engaging with teeth of a rack provided around a surface of the dose knob, which teeth are free to flex inwardly when the button is depressed. The button may further comprise means for inducing rotation of the dose knob in a dose reducing direction when the button is depressed, and means for defining the dose reducing steps. These means may be provided by an indexing finger depending from the user actuable button and which engages a rack formed around a surface of the dose knob.

In order to assist a user who requires more than one type of medicament, the apparatus may further comprise an annular member that is removably attachable to an outer surface of the main body, the annular member being used to identify a medicament.

According to a second aspect of the present invention there is provided medication delivery apparatus for receiving a medication containing member, the apparatus comprising:
 spring means for storing a force which when released causes ejection of the medication from a received medication containing member;
 a dose knob which when rotated in a first direction moves the spring to a force storing position, the dose setting knob providing a plurality of discrete setting positions corresponding to respective doses;
 a user actuable trigger for releasing said stored force to eject medication from said medication containing member; and
 a user actuable button arranged to reduce a stored force in the spring without causing ejection of medication from said medication containing member.

Preferably, the apparatus comprises a drive means for engaging a medication containing chamber, and a drive shaft coupled between the drive means and said spring means. In a resting state, the dose knob is coupled to the drive shaft for rotation therewith. When the button is depressed, the dose knob is at least temporarily uncoupled from the drive shaft to allow the dose knob to rotate relative to the drive shaft.

According to a third aspect of the present invention there is provided a method of setting a dose of medication to be ejected from a medication containing member received within a dose delivery apparatus, the method comprising:
 rotating a dose knob of the apparatus in a first direction to one of a plurality of discrete positions corresponding to respective doses; and
 changing the set dose to a reduced dose by depressing a button one or more times.

According to a fourth aspect of the present invention there is provided medication delivery apparatus comprising:
- a housing for receiving a medication containing member;
- a drive member mounted within the housing for engaging with the medication containing member and moveable axially within the housing;
- a spring contained within the housing and coupled to the drive member;
- a dose setting knob coupled to said spring, and rotatably coupled to the housing such that rotation of the knob relative to the housing in a first direction results in compression or twisting of the spring;
- spring retaining means comprising a toothed rack coupled to one of the housing and the dose knob and at least one spring mounted tooth coupled to the other of the housing and the dose knob, the or each tooth engaging the toothed rack to prevent a force stored on the spring from moving the spring to release the force, whilst allowing a user to rotate the dose knob in a second, reverse direction, to reduce a set dose; and
- a user actuable trigger for releasing the spring to push the drive member through the housing.

In a preferred embodiment of the invention, the or each spring mounted tooth has a one piece moulded construction, with a tooth element mounted on an end of a moulded spring.

Preferably, the apparatus comprises an elongate drive shaft coupling said spring to said drive member. An end of the drive shaft is coupled to the dose knob for rotation therewith. The other end of the drive shaft provides part of said spring retaining means, either said at least one sprung tooth or said toothed rack. The other of said at least one sprung tooth and said toothed rack is provided on a drive element which is coupled to the housing via said user actuable trigger. The drive element is in turn coupled to the drive member. Actuation of the trigger releases the drive element to rotate within the housing under the action of the spring via the drive shaft. Rotation of the drive element produces axial movement of the drive member through the housing.

According to a fifth aspect of the present invention there is provided medication delivery apparatus comprising:
- a housing for receiving a medication containing member;
- a drive member mounted within the housing for engaging with the medication containing member and moveable axially within the housing;
- a torsion spring contained within the housing and coupled to the drive member;
- a dose setting knob coupled to said spring, and rotatably coupled to the housing such that rotation of the knob relative to the housing in a first direction results in loading of the spring;
- a user actuable trigger for releasing the spring to push the drive member through the housing; and
- a rotatably mounted visual indicator for indicating the dose to be delivered, the rotatably mounted visual indicator being rotatable over at least one complete revolution.

According to a sixth aspect of the present invention, there is provided medication delivery apparatus comprising:
- a housing for receiving a medication containing member;
- a drive member mounted within the housing for engaging with the medication containing member and moveable axially within the housing;
- a torsion spring contained within the housing and coupled to the drive member;
- a dose setting knob coupled to said spring, and rotatably coupled to the housing such that rotation of the knob relative to the housing in a first direction results in loading of the spring;
- a dial cam configured to co-operate with a dial key, such that upon rotation of the dose setting knob, the dial cam and the dial key co-operate to strain or release the torsion spring, depending upon the direction of rotation of the dose setting knob.

BRIEF DESCRIPTION OF THE DRAWINGS

For a better understanding of the present invention and in order to show how the same may be carried into effect reference will now be made by way of example to the accompanying drawings in which:

FIG. 2 shows a horizontal cross-section through the injector of FIG. 1;

FIG. 3 shows a vertical cross-section through the injector of FIG. 1;

DETAILED DESCRIPTION

Figure 1:
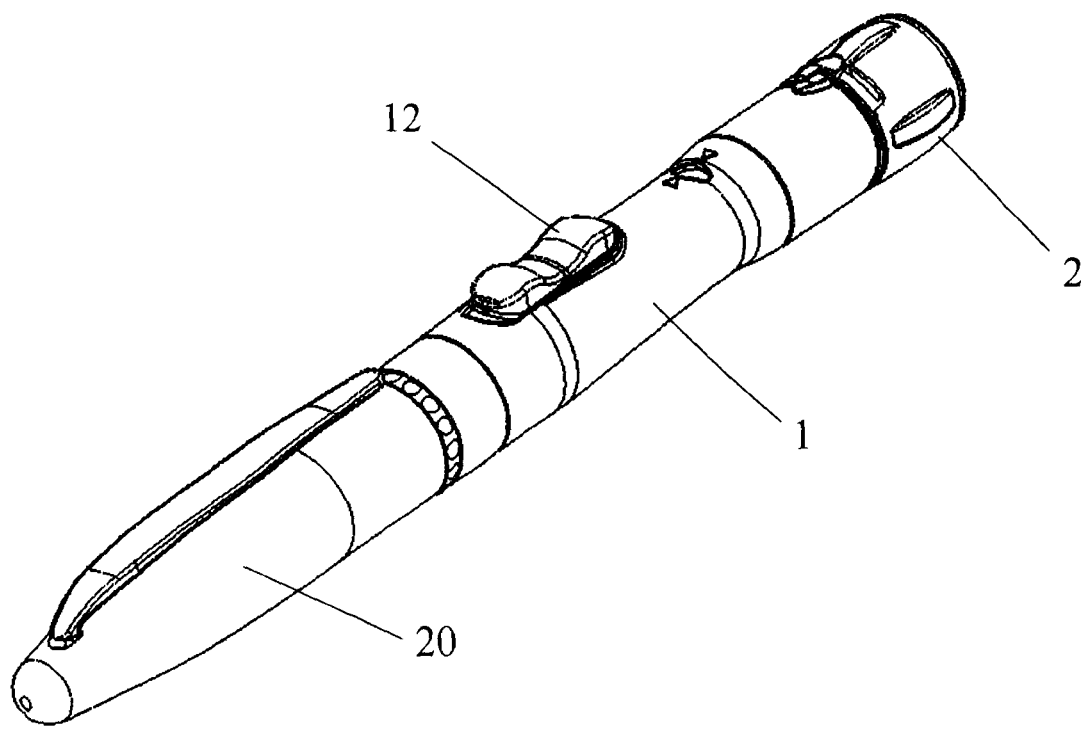
FIG. 1 shows schematically a pen-type injector.
Figure 2A:
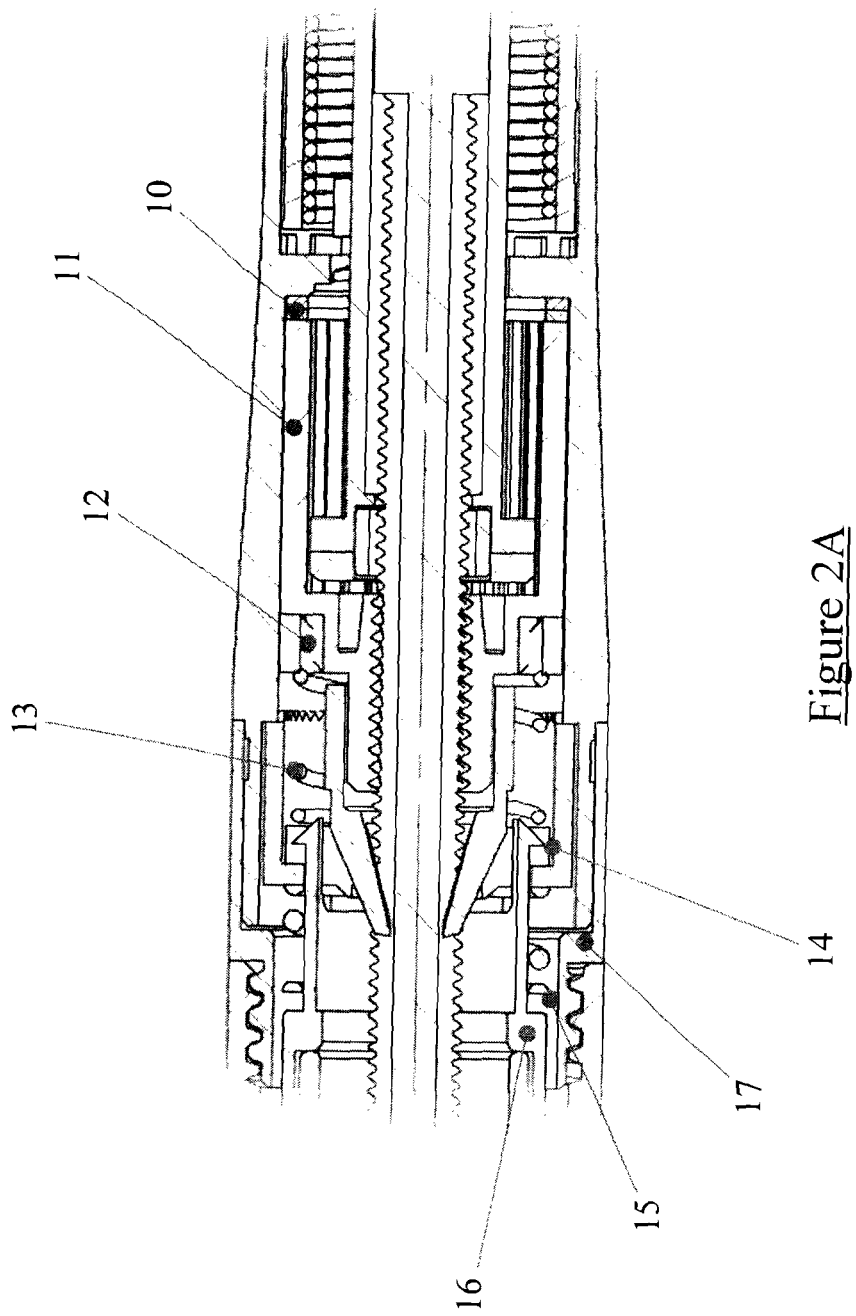
FIG. 2A shows an enlarged view of a retaining and trigger portion of the injector taken at A of FIG. 2.
Figure 4:
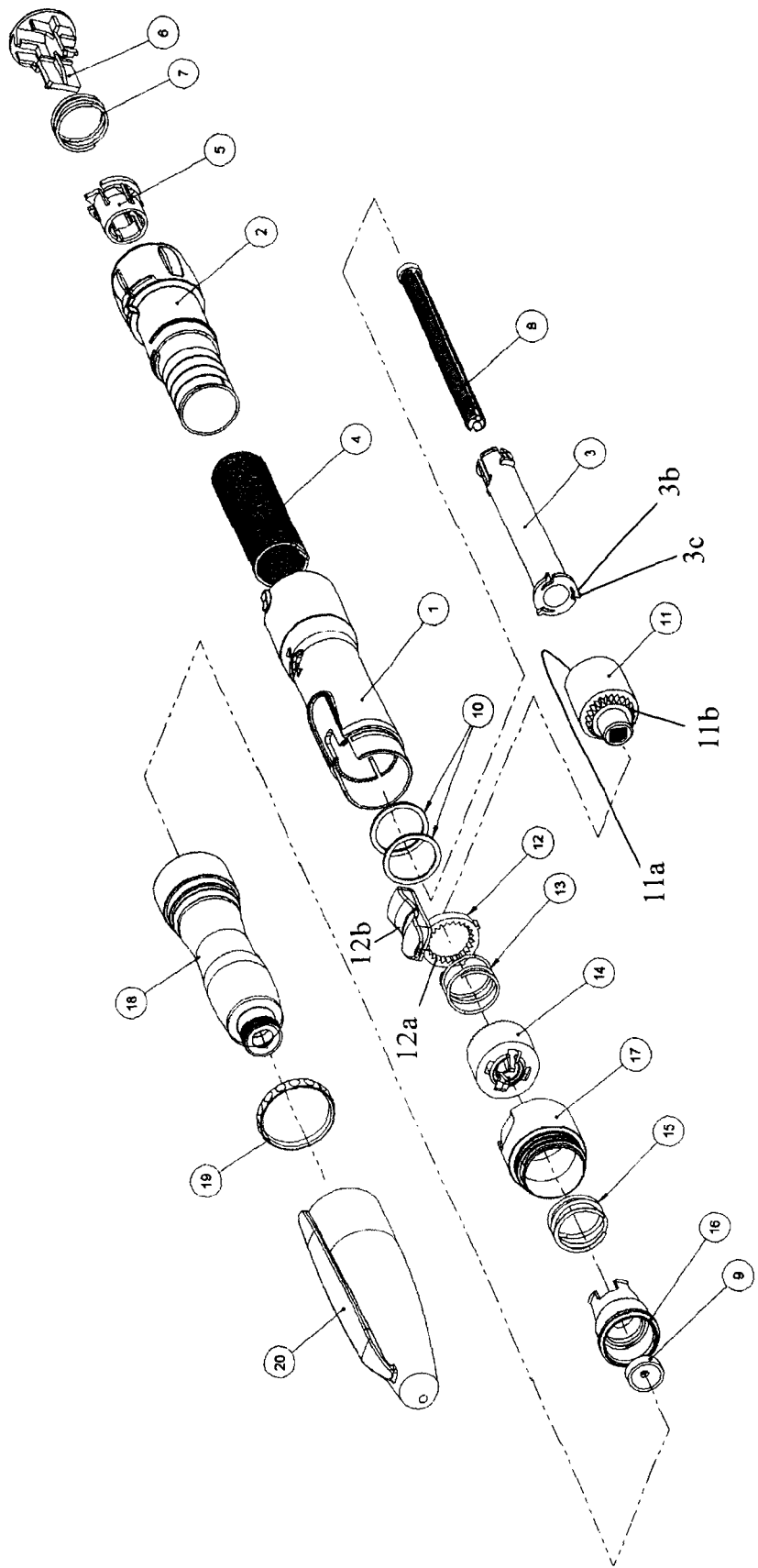
FIG. 4 is a perspective exploded view of the injector of FIG. 1.
Figure 5:
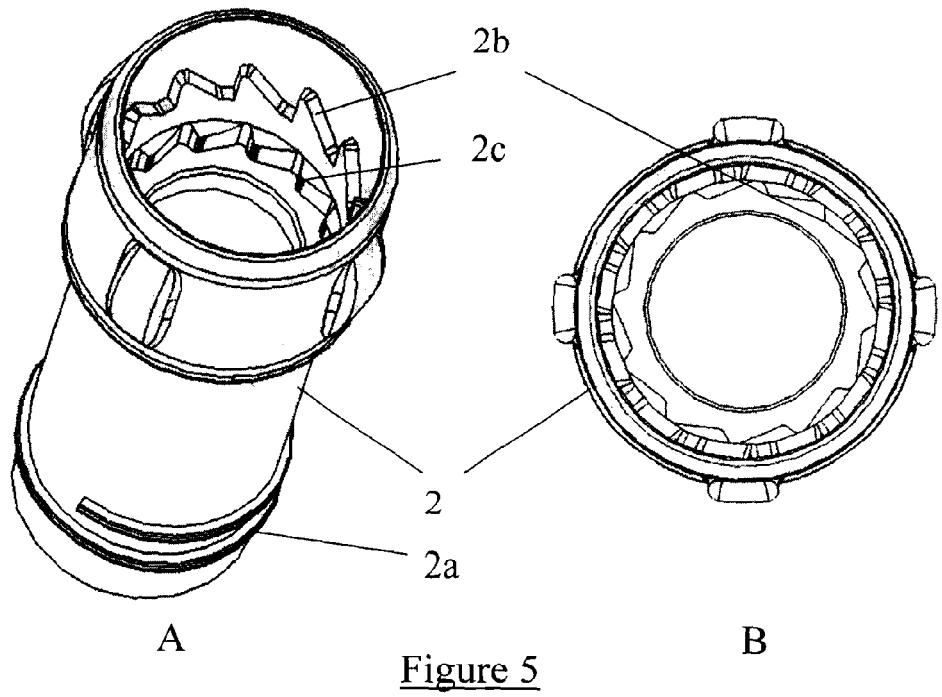
FIG. 5 shows a dose knob of the injector of FIG. 1.
Figure 6:
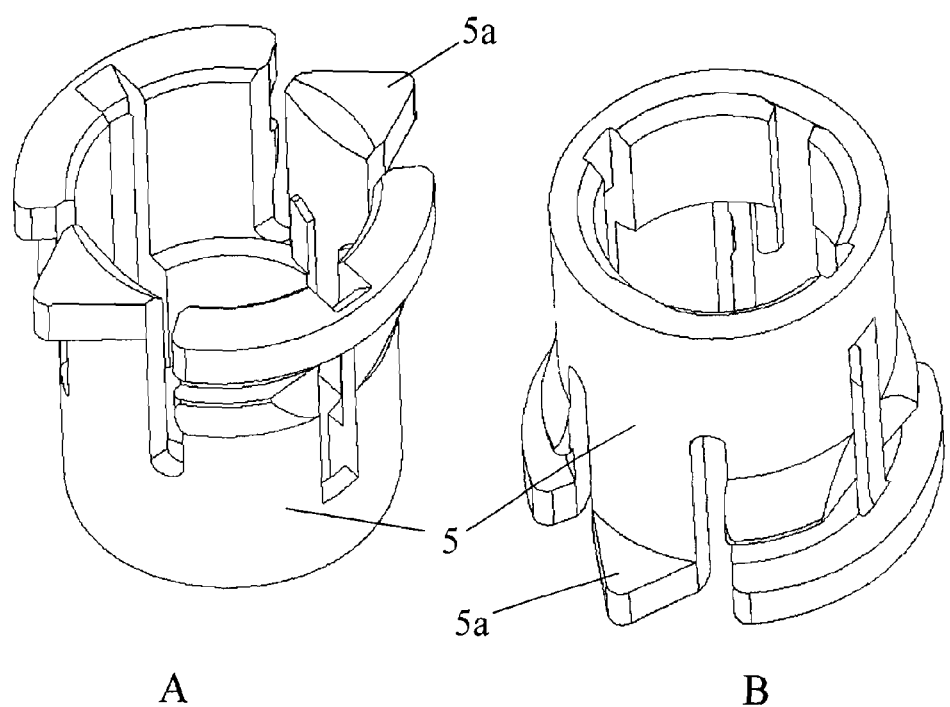
FIG. 6 shows a clutch collet of the injector of FIG. 1.

There is illustrated in FIG. 1 a pen-type injector having a user operable dose setting mechanism. With reference to FIGS. 2 to 7, it can be seen that the injector comprises a main body 1 and a cap 20 which snap fit together. Identity ring 19 is colour coded to indicate the type of medicament to be delivered by the injector. A screw thread is provided on an inner surface of the main body 1 at its upper end. This internal screw thread is engaged by an external screw thread 2a provided on an outer surface of a dose knob 2. The dose knob 2 is illustrated in detail in FIG. 5. Longitudinal movement of the dose knob 2 within the pen body 1 is limited in both directions.

A cartridge housing 18 is secured to a lower end of the main body 1 and is arranged to receive a disposable medication filled cartridge (not shown). Such a cartridge has a rubber bung sealing one end of the cartridge, with the other end being arranged to receive a disposable needle. The cartridge is typically multi-use, with a user attaching a new needle for each injection.

A torsion spring 4 is located coaxially within the main body 1 and is arranged to provide the drive force for ejecting medication from a loaded cartridge. The spring 4 is fixed at its upper end to the dose knob 5. At its lower end, the spring 4 is fixed to the housing via a retaining ring moulded integrally with the housing 1.

A generally cylindrical ratchet drive shaft 3 extends through the centre of the spring 4. An enlarged end portion 3a of the shaft 3 has three sprung legs 3b formed around its periphery, the legs being spaced equiangularly around the shaft. At the outermost end of each leg, a tooth 3c is provided. The teeth 3c engage teeth of a rack 11a (not visible in FIG. 4) formed around the inner surface of a generally cylindrical drive gear component 11 which sits within the main body 1 at a fixed axial position. The drive gear 11 has a second toothed rack 11b formed around a lower outer surface portion. This rack sits within a correspondingly sized rack 12a formed on an inner surface of a retaining ring 12. The ring 12 is formed integrally with a trigger 12b, with the component being slidably mounted within a slot formed in the main body 1, separated from the body by a pair of thrust washers 10. A spring 13 urges the trigger 12b in an upward direction, maintaining the racks 11b, 12a in locking engagement in the absence of a user force applied to the trigger. The dose knob 2 and the trigger 12b may be provided with a soft rubber over-molding. This provides the user with a more comfortable and better grip.

Considering further the ratchet drive shaft 3, this is coupled at its upper end to a clutch collet 5. The clutch collet, illustrated in FIG. 6 (viewed from above A and below B) rotates with the drive shaft 3 and is provided with a pair of sprung fingers 5a. The sprung fingers are shaped in cross-section to provide respective teeth for engaging teeth of a rack 2c formed around an inner surface of the dose knob 2. The fingers 5a are biased outwardly.

Figure 7:
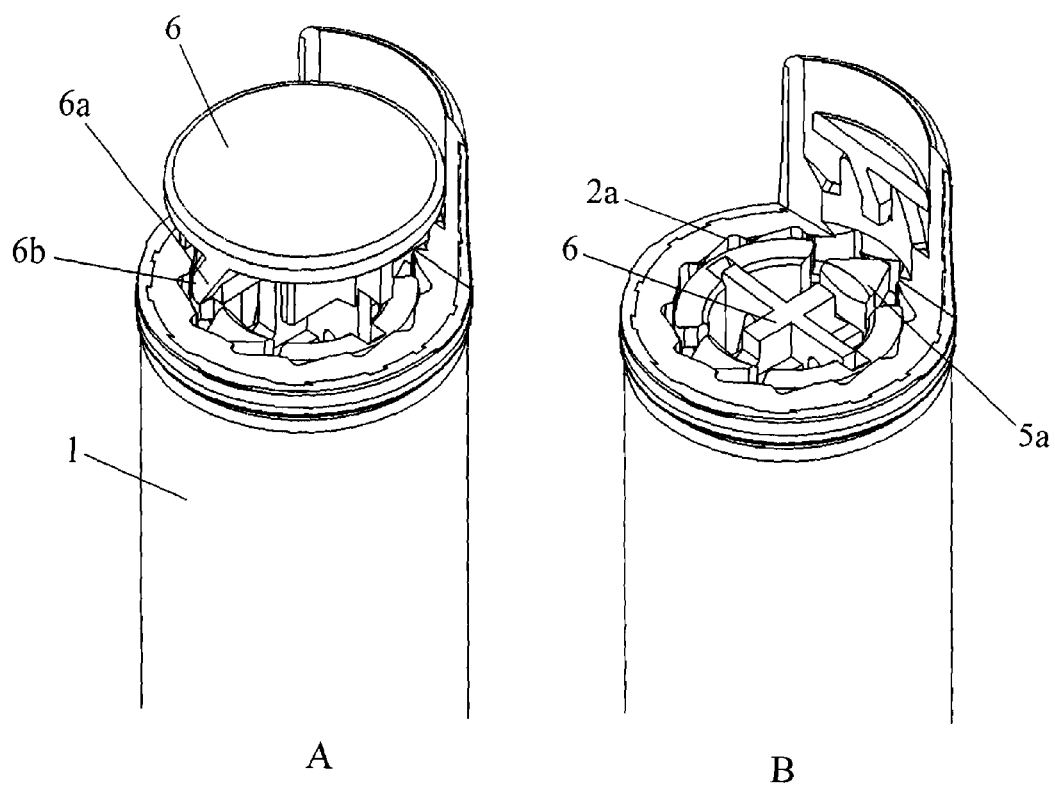
FIG. 7 shows in partial cross-section of an end of the injector of FIG. 1.
Figure 8:
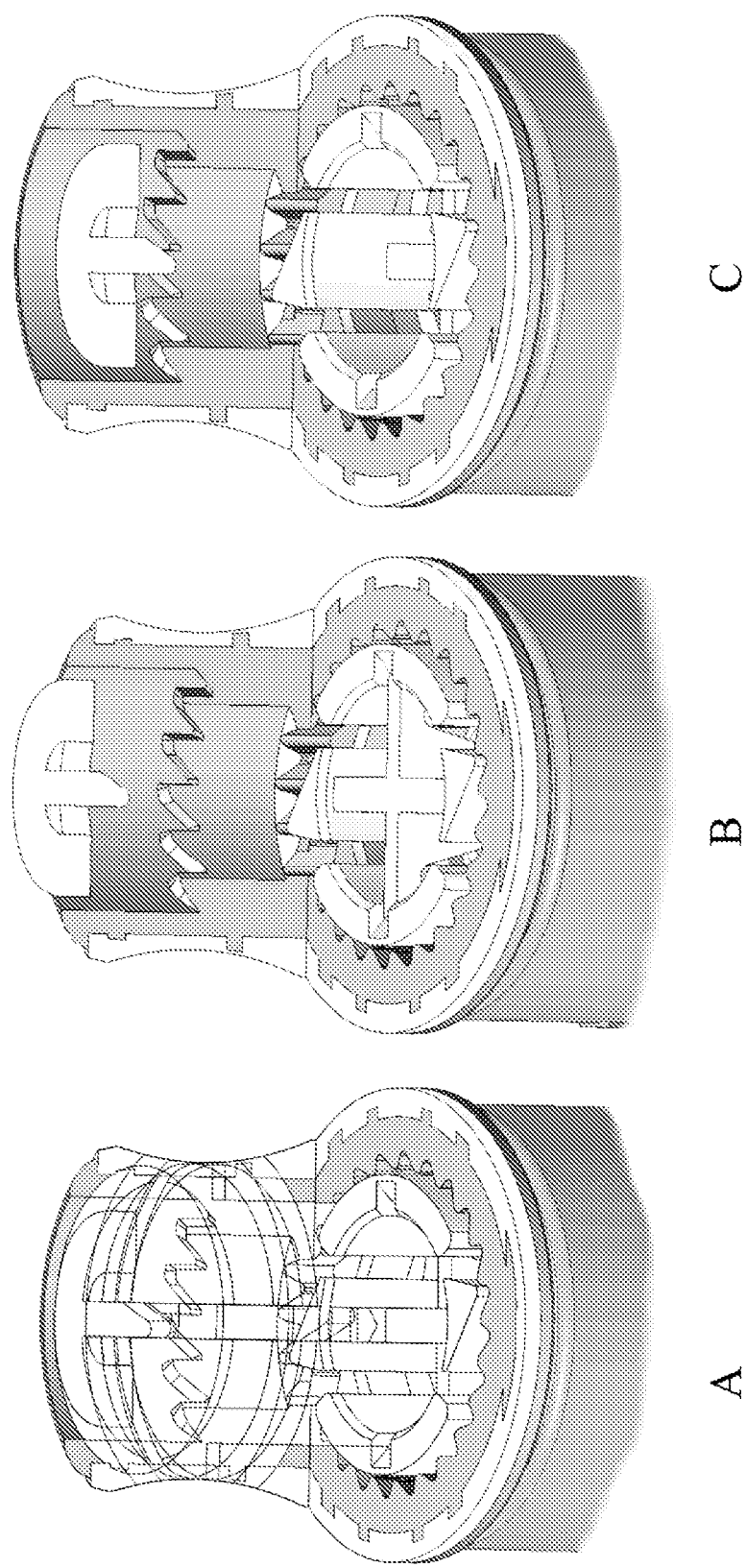
FIG. 8 illustrates an operating sequence of the injector of FIG. 1.
Figure 9:
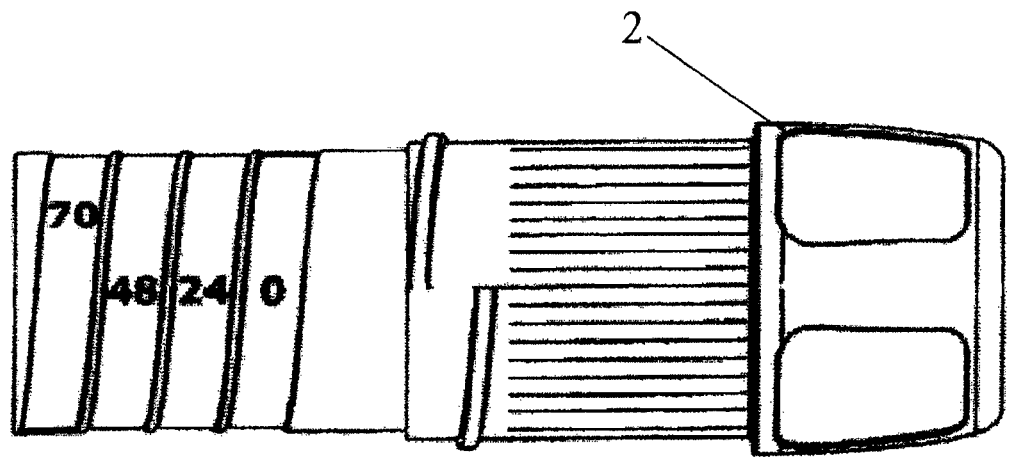
FIG. 9 shows a horizontal side elevation view of a dose knob

A rewind button 6 is located within the dose knob 2, projecting therefrom. The button 6 is coupled to the ratchet drive shaft 3, rotating with the drive shaft but being able to slide longitudinally within the drive shaft. A spring 7 is coupled between the button 6 and the drive shaft 3 and biases the button outwardly relative to the main body 1. The lower portion of the button 6 is generally cross-shaped, with two opposed arms of the cross opposing the sprung fingers 5a of the clutch collet 5. These arms taper inwardly such that they prevent any radially inward flexing of the sprung fingers 5a when the button is in its outer position, whilst allowing inward flexing when the button is fully depressed against the bias of the button spring 7. This arrangement is best illustrated in FIG. 7, where FIG. 7A illustrates the button 6 in situ whilst FIG. 7B illustrates the end of the injector with a cross-section taken through the button 6.

A leadscrew 8 has a screw thread formed along the length of its outer surface. The leadscrew is located within the ratchet drive shaft 3, and engages a complimentary screw thread formed on the inner surface of the drive gear 11. The end portion of the leadscrew 8 projecting from the ratchet drive shaft 3 has a leadscrew cap secured thereto. Rotational movement of the leadscrew relative to the drive shaft is prevented by the engagement of recesses formed along the length of the leadscrew with complimentary splines provided on an inner surface of a locking bush 14. The locking bush is held within a mid-body compartment 17 which itself is secured to the end of the main body 1 via a pair of complimentary screw threads. On coupling with a medicament containing cartridge, the cartridge compression cup 16 will compress the spring 15 and transmit the loading onto the locking bush 14. The serrated edge of the locking bush engages with the mating features of the body 1 preventing the locking bush from rotating and ensuring that the leadscrew 8 moves forward when subjected to rotation following release of the drive gear 11.

An indexing finger 6a depends from an inner surface of the button 6. The finger is provided at its end with a ramp shaped tooth 6b having a vertical, blocking surface and a sloping drive surface. The tooth 6b engages teeth of an indexing rack 2b formed around an inner surface of the dose knob 2, when the button is pressed into the dose knob 2.

In order for a user to set the amount of medicament to be delivered, the dose knob 2 has a barrel 2d formed integrally with the dose knob 2. The barrel 2d has a series of numbers printed around its circumference, so that as the dose knob 2 is rotated, the barrel 2d also rotates. A window in the main body 1 allows the user to see one of the printed numbers, and the printed number relates to the amount of medicament that will be delivered.

Figure 13:
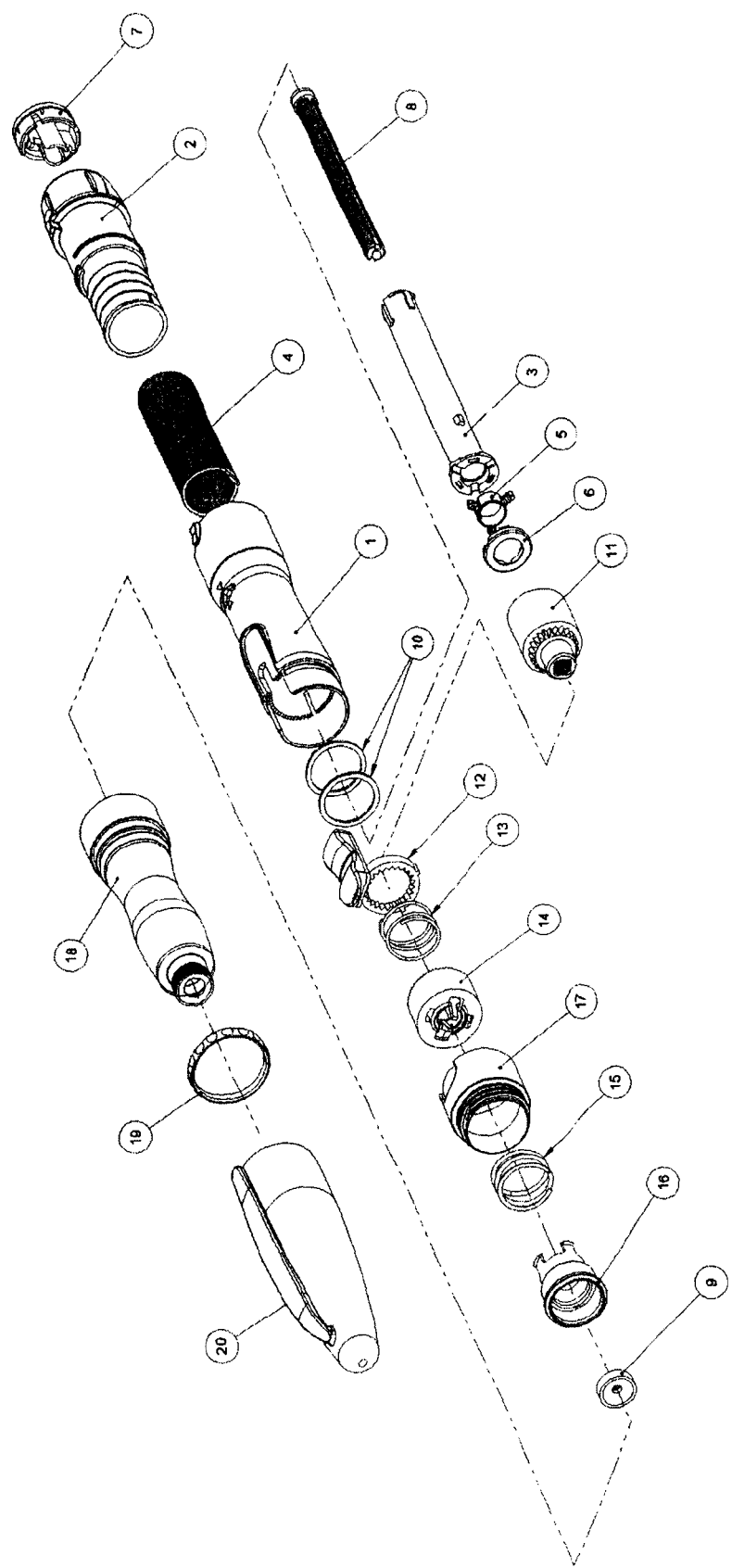
FIG. 13 is a perspective exploded view of the injector of FIG. 9.

When the dose knob 2 is rotated, screw thread 2d ensures that the dose knob moves linearly with respect to the longitudinal axis of the main body 1, and allows the dose knob to be rotated over more than one revolution. This allows both higher loading of the torsion spring, and also allows the barrel 2d to indicate doses over more than one revolution of the barrel, provided that the printed numbers relating to a medicament dose setting are printed in a helical pattern around the outer surface of the barrel 2d, as shown in FIG. 13.

Figure 10:
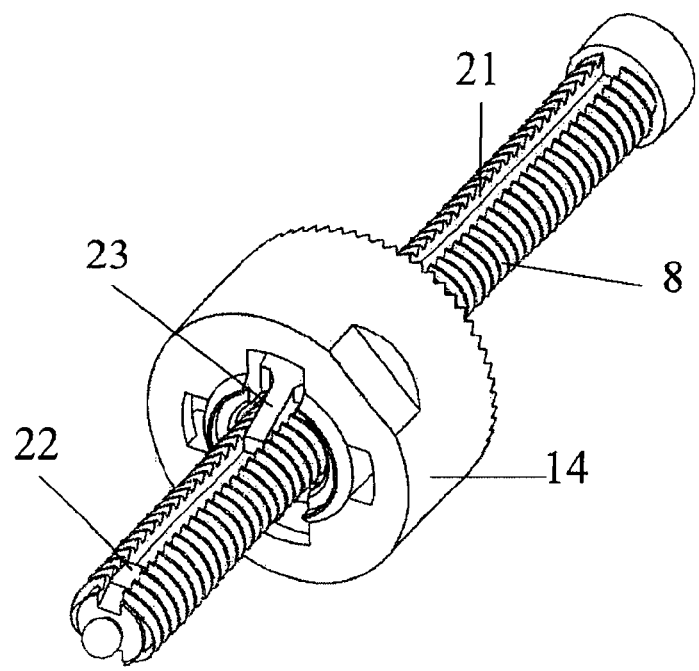
FIG. 10 is a perspective view of a locking bush and a leadscrew.
Figure 11:
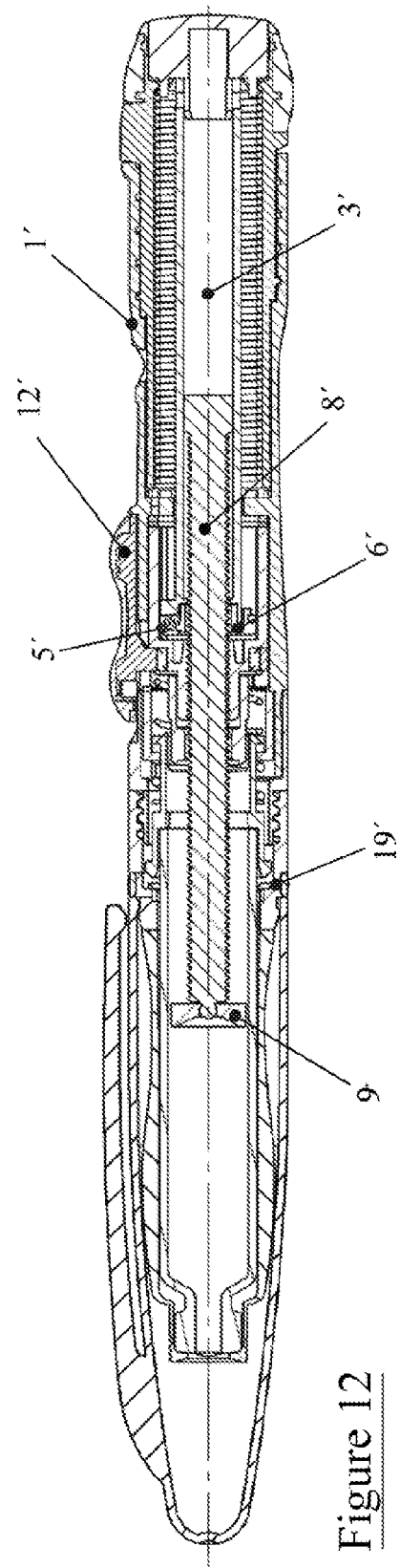
FIG. 11 shows a horizontal cross-section through an alternative internal construction of the injector.
Figure 12:
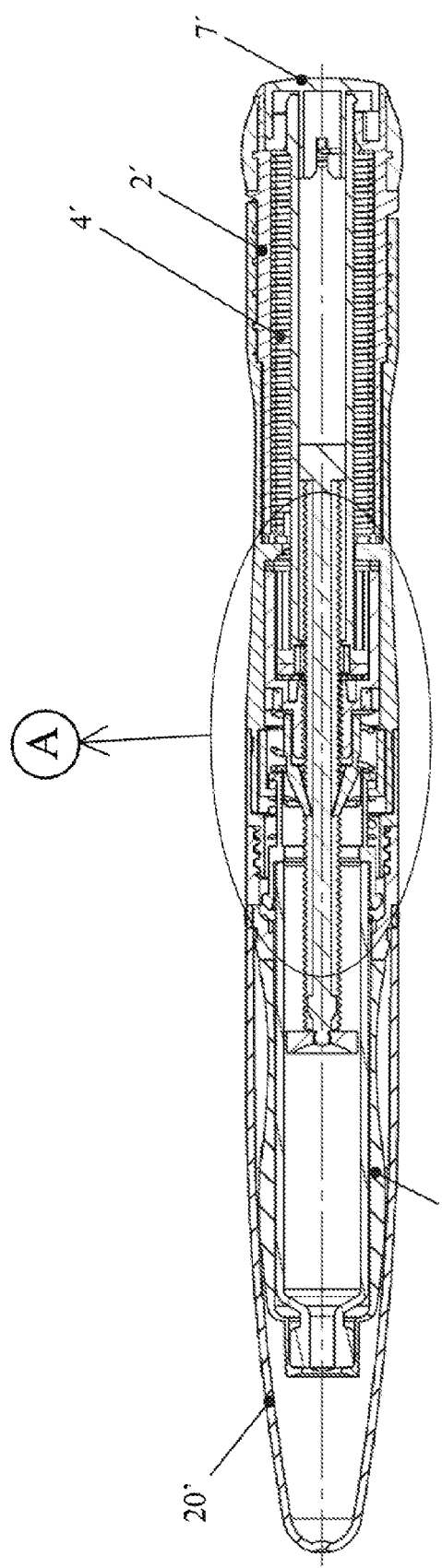
FIG. 12 shows a vertical cross-section through the alternative injector of FIG. 9.
Figure 11A:
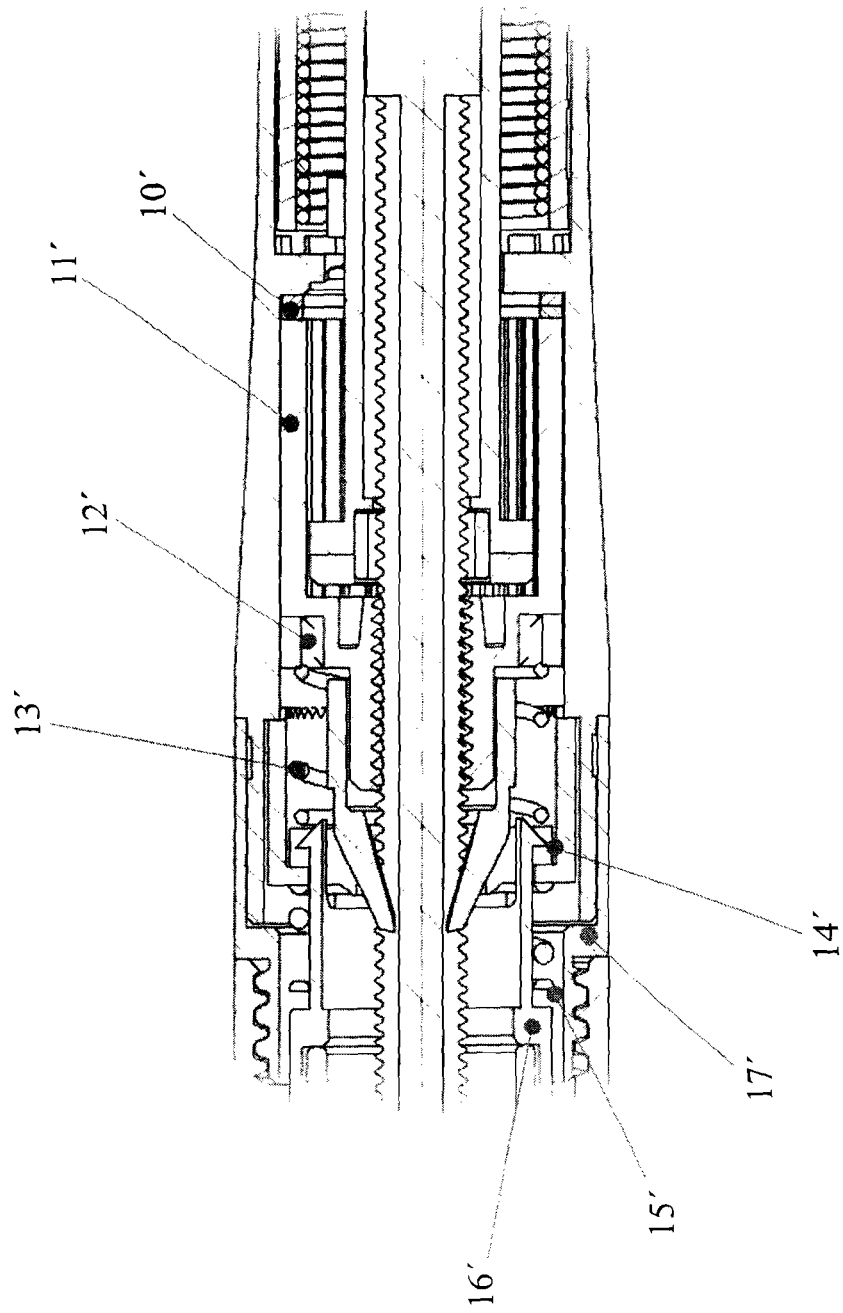
FIG. 11A shows an enlarged view of a retaining and trigger portion of the injector taken at A of FIG. 11.

As shown in FIG. 10, the leadscrew 8 comprises a pair of channels 21 running along its longitudinal axis. At one end of each channel is a ramp 22. The locking bush 14 comprises a pair of fingers 23 that engage with a corresponding leadscrew channel 21. This ensures that when the device is assembled, the leadscrew 8 and the locking bush 14 are located correctly together. The fingers 23 are flexible such that when the leadscrew is passed through the centre of the locking bush 14, the fingers ride up the corresponding ramps 22 and flex outwards. Once the fingers 23 have passed over the ramps 22, they snap into engagement with the channels 21. During resetting, the fingers 23 abut against the corresponding ramps 22 to ensure that the locking bush 14 does not move out of engagement with the leadscrew 8.

A full list of injector components with their reference numbers as shown in FIGS. 1 to 8 is contained within Table 1 below.

Considering now the operation of the injector, a user sets a dose by rotating the dose knob 2 in a clockwise direction. As the dose knob 2 is rotated, the top of the spring 4 rotates with it creating torsion of the spring. Engagement of the sprung fingers 5a at the top of the ratchet drive shaft 3 with the rack 2c formed on the inner surface of the dose knob 2 also causes the ratchet drive shaft 3 to rotate. At the lower end of the ratchet drive shaft 3, the teeth of the sprung legs 5a "click" around the teeth of the rack 11a. The engagement of the teeth with the rack 11a prevents the spring 4 unwinding after each click. Each click corresponds to a predefined angular rotation of the spring and therefore to a predefined ejection dose. It will be readily appreciated that, during the dose setting action, the drive gear 11 is not rotated so no axial movement of the leadscrew 8 is induced. No medication is therefore ejected from the cartridge during the dose setting operation (or indeed air introduced due to back filling).

When the user applies a downward force to the trigger 12b, this disengages the racks of the trigger 12b and the drive gear 11. This frees the drive gear 11 and the torsion spring 4 to rotate. As the drive gear 11 rotates about the leadscrew 8, the leadscrew is driven down through the drive gear causing the leadscrew cap 9 to push the bung of the cartridge through the cartridge body, expelling medication from the cartridge through the attached syringe.

In the event that a user oversets a dose, i.e. over-rotates the dose knob 2, the user fully presses the button 6 into the dose knob 2 against the action of the biasing spring 7. As the button 6 is depressed, the drive surface of the tooth 6b comes into contact with one of the teeth formed on the indexing rack 2b (from the starting position of FIG. 8A to the position shown in FIG. 8B). Further pressure induces a rotational force on the dose knob 2 in the counter-clockwise direction until the fully depressed position of FIG. 8C is reached. At substantially the same time, the downward movement of the cross-arms of the button 6 results in the sprung fingers 5a being free to flex inwardly, freeing the dose knob 2 and the spring 4 to rotate under one or both of the force stored in the spring and the force induced by the tooth. The dose knob 2 is able to rotate until the blocking surface of the tooth engages the next stop surface of the upper rack. Neither the ratchet drive shaft 3 nor the drive gear 11 rotate during this resetting operation. No axial movement of the leadscrew 8 is therefore induced and no medication ejected from the cartridge. The dose resetting mechanism operates by temporarily decoupling the dose knob and the torsion spring from the ratchet drive shaft allowing the former to rotate relative to the drive shaft. Upon removal of the pressure from the button 6, the rewind button spring 7 returns the button to its outermost position, whereupon the teeth of the sprung fingers 5a reengage with the teeth of the rack 2c.

An alternative pen-type injector will now be described with reference to FIGS. 11 to 14. Externally, this injector has a similar external appearance to the injector illustrated in FIG. 1. The operating principle of the alternative injector is similar to that of the injector of FIGS. 2 to 10 in terms of both the dose setting and firing functionality. However, the dose resetting mechanism differs.

Figure 14:
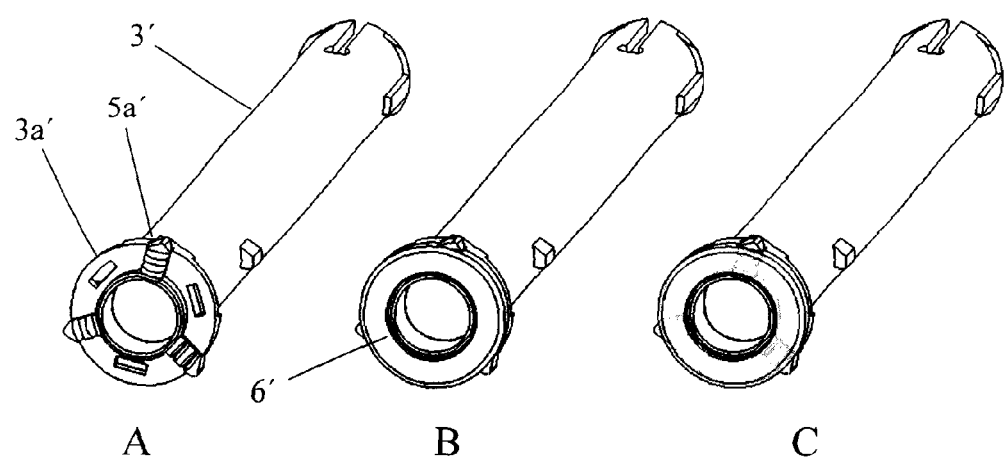
FIG. 14 shows perspective views of an end of a drive shaft of the injector of FIG. 9.

The injector comprises a dose setting knob 2' which is coupled to the main body 1' via complimentary screw threads. The end of the dose knob 2' is closed by a dose knob cap 7' which rotates with the dose knob. Considering now the ratchet drive shaft 3', this has an end collar 3a' having three radial extending slots formed therein (FIG. 14, where FIG. 14A shows the knob 2 with a ratchet retainer removed, FIG. 14B shows the knob with the retainer in situ, and FIG. 14C shows the knob with the retainer in place but shown transparent). These slots receive respective arms (also referred to as a dial key) 5a' of a ratchet plunger component 5' having a cylindrical body. The body sits tightly within the circular opening in the end of the collar 3a'. Each arm 5a' comprises a moulded spring body and an end tooth, the surfaces of the tooth sloping at the same angle. A ratchet retainer 6' snaps over the end of the collar 3a' to secure the ratchet plungers in place. The teeth of the ratchet plunger project from the ends of their respective slots by approximately 0.5 mm, and can be deflected radially inwards (by approximately 0.25 mm) as a result of the moulded springs.

In the assembled injector, the teeth of the ratchet plunger 5' engage the rack (also referred to as a dial cam) formed around the inner surface of the drive gear 11'. The teeth surfaces of the rack are also equiangular, corresponding to the teeth of the ratchet plunger.

A full list of injector components with their reference numbers as shown in FIGS. 11 to 14 is contained within Table 2 below.

In use, a user dials up a dose by rotating the dose knob 2' in a clockwise direction. The user applied force is sufficient to overcome the resistance between the teeth of the ratchet plunger 11' and those of the rack of the drive gear 11', the drive gear being held in place against rotation by the trigger 12'. During this action, the teeth of the ratchet plunger are pushed inward into the end collar of the ratchet drive shaft to allow them to ride over the teeth of the rack within the drive gear. In the same way, if a user wishes to reduce a set dose, he or she rotates the dose knob in an anti-clockwise direction. The shape of the ratchet plunger teeth permits this. Thus according to this design, there is no need for a rewind button separate from the dose knob in order to facilitate resetting of the dose.

It will be appreciated by the person of skill in the art that various modifications may be made to the above described embodiments without departing from the scope of the present invention.

TABLE 1

| Reference numeral | Description |
| --- | --- |
| 1 | Main Body |
| 2 | Dose Knob - Rewind Button |
| 3 | Ratchet Drive Shaft - No Rewind |
| 4 | Torsion Spring - Rewind Button |
| 5 | Clutch Collet |
| 6 | Rewind Button |
| 7 | Rewind Button Spring |
| 8 | Leadscrew |
| 9 | Leadscrew Cap |
| 10 | Thrust Washer |
| 11 | Drive Gear - No Rewind (1 Unit) |
| 12 | Trigger |
| 13 | Trigger Spring |
| 14 | Locking Bush |
| 15 | Compression Cup Spring |
| 16 | Cartridge Compression Cup |
| 17 | Mid-Body |
| 18 | Cartridge Housing |
| 19 | Identity Ring |
| 20 | Cap |
| 21 | Leadscrew channel |
| 22 | Leadscrew ramp |
| 23 | Locking bush finger |

TABLE 2

| Reference numeral | Description |
| --- | --- |
| 1 | Main Body |
| 2 | Dose Knob |
| 3 | Ratchet Drive Shaft |
| 4 | Torsion Spring |
| 5 | Ratchet Plungers |
| 6 | Ratchet Retainer |
| 7 | Dose Knob Cap |
| 8 | Leadscrew |
| 9 | Leadscrew Cap |
| 10 | Thrust Washer |
| 11 | Drive Gear |
| 12 | Trigger |
| 13 | Trigger Spring |
| 14 | Locking Bush |
| 15 | Compression Cup Spring |
| 16 | Cartridge Compression Cup |
| 17 | Mid-Body |
| 18 | Cartridge Housing |
| 19 | Identity Ring |
| 20 | Cap |

The invention claimed is:

1. A medication delivery apparatus comprising:
   a housing for receiving a medication containing member;
   a drive member mounted within the housing for contacting and engaging with the medication containing member and moveable axially within the housing;
   a spring contained within the housing and coupled to the drive member;
   a dose setting knob coupled to said spring, and rotatably coupled to the housing such that rotation of the knob relative to the housing in a first direction results in compression or twisting of the spring;

a user actuable trigger for releasing the spring to push the drive member through the housing; and a user actuable button coupled to said housing for axial motion relative thereto, said button being coupled to said spring to cause the spring to unwind or expand without causing any substantial movement of said drive member.

2. The apparatus according to claim 1, wherein actuation of said button causes said spring to unwind or expand in discrete steps with each press of the button.

3. The apparatus according to claim 1 further comprising a drive shaft extending through the housing, the drive shaft being coupled via a ratchet mechanism to a drive element where the drive element is prevented from moving axially within the housing, and the drive element being coupled to said drive member, whereby rotation of the drive element gives rise to axial movement of the drive member.

4. The apparatus according to claim 1, comprising a drive shaft extending through the housing, the drive shaft being coupled via a ratchet mechanism to a drive element where the drive element is prevented from moving axially within the housing, and the drive element being coupled to said drive member, whereby rotation of the drive element gives rise to axial movement of the drive member, wherein said dose setting knob is coupled to the drive shaft for rotation therewith when the user actuable button is in a released position, and is decoupled from the drive shaft when the button is in a depressed position whereupon the dose knob is able to rotate relative to the drive shaft.

5. The apparatus according to claim 1 and comprising a drive shaft extending through the housing, the drive shaft being coupled via a ratchet mechanism to a drive element where the drive element is prevented from moving axially within the housing, and the drive element being coupled to said drive member, whereby rotation of the drive element gives rise to axial movement of the drive member, wherein said user actuable trigger is configured to release said drive element for rotation by the spring when the trigger is actuated, and to secure the drive element when the trigger is in its resting state.

6. The apparatus according to claim 1, wherein actuation of said button causes said spring to unwind or expand in discrete steps with each press of the button, said ratchet mechanism comprising two complimentary sets of teeth, a first set formed on an end of the drive shaft and a second formed on the drive element, wherein with the trigger in its resting state, the teeth of the drive shaft are able to ride over the teeth of the drive unit to allow rotation of the drive shaft relative to the drive element when the dose knob is rotated in a dose setting direction.

7. The apparatus according to claim 1, wherein actuation of said button causes said spring to unwind or expand in discrete steps with each press of the button, said user actuable button being coupled to the drive shaft for rotation therewith.

8. The apparatus according to claim 1, wherein actuation of said button causes said spring to unwind or expand in discrete steps with each press of the button, said user actuable button being coupled to the drive shaft for rotation therewith, and the drive shaft comprising means for locking the drive shaft to the dose knob, which means is released when the button is depressed by a user.

9. The apparatus according to claim 1, wherein actuation of said button causes said spring to unwind or expand in discrete steps with each press of the button, said user actuable button being coupled to the drive shaft for rotation therewith; and the drive shaft comprising means for locking the drive shaft to the dose knob, which means is released when the button is depressed by a user; and the locking means comprising one or more teeth for engaging with teeth of a rack provided around a surface of the dose knob, which teeth are free to flex inwardly when the button is depressed.

10. The apparatus according to claim 1, the button comprising means for inducing rotation of the dose knob in a dose reducing direction when the button is depressed, and means for defining the dose reducing steps.

11. The apparatus according to claim 1, the button comprising means for inducing rotation of the dose knob in a dose reducing direction when the button is depressed, and means for defining the dose reducing steps, said means for inducing rotation and for defining the dose reducing steps comprising an indexing finger depending from the user actuable button and which engages a rack formed around a surface of the dose knob.

12. The apparatus according to claim 1, further comprising an annular member that is removably attachable to an outer surface of the main body, the annular member being used to identify a medicament.

13. A medication delivery apparatus comprising:

a housing for receiving a medication containing member;

a drive member mounted within the housing for contacting and engaging with the medication containing member and moveable axially within the housing;

a spring contained within the housing and coupled to the drive member;

a dose setting knob coupled to said spring, and rotatably coupled to the housing such that rotation of the knob relative to the housing in a first direction results in compression or twisting of the spring;

spring retaining means comprising a toothed rack coupled to one of the housing and the dose knob and at least one spring mounted tooth coupled to the other of the housing and the dose knob, the or each tooth engaging the toothed rack to prevent a force stored on the spring from moving the spring to release the force, whilst allowing a user to rotate the dose knob in a second, reverse direction, to reduce a set dose; and a user actuable trigger for releasing the spring to push the drive member through the housing.

14. The apparatus according to claim 13, wherein the or each spring mounted tooth has a one piece moulded construction, with a tooth element mounted on an end of a moulded spring.

15. The apparatus according to claim 13 and comprising an elongate drive shaft coupling said spring to said drive member, wherein an end of the drive shaft is coupled to the dose knob for rotation therewith.

16. The apparatus according to claim 13 and comprising an elongate drive shaft coupling said spring to said drive member, wherein an end of the drive shaft is coupled to the dose knob for rotation therewith, and wherein the other end of the drive shaft provides part of said spring retaining means, either said at least one sprung tooth or said toothed rack, and the other of said at least one sprung tooth and said toothed rack is provided on a drive element which is coupled to the housing via said user actuable trigger, the drive element in turn being coupled to the drive member, wherein actuation of the trigger releases the drive element to rotate within the housing under the action of the spring via the drive shaft, and rotation of the drive element produces axial movement of the drive member through the housing.

* * * * *